United States Patent [19]
Von Itzstein et al.

[11] Patent Number: 5,639,786
[45] Date of Patent: Jun. 17, 1997

[54] ANTIVIRAL 4-SUBSTITUTED-2-DEOXY-2,3-DIDEHYDRO-DERIVATIVES OF α-D-NEURANINIC ACID

[75] Inventors: Laurence Mark Von Itzstein; Wen-Yang Wu; Tho Van Phan; Basil Danylec; Betty Jin, all of Victoria, Australia

[73] Assignee: BIOTA Scientific Management, Pty., Ltd., Victoria, Australia

[21] Appl. No.: 267,309

[22] Filed: Jun. 29, 1994

Related U.S. Application Data

[63] Continuation of Ser. No. 984,124, Dec. 4, 1992, abandoned.
[51] Int. Cl.⁶ ............ A61K 31/35; C07D 309/28
[52] U.S. Cl. .................... 514/459; 549/424
[58] Field of Search .............. 549/424; 514/459

[56] References Cited

PUBLICATIONS

Schreiner et al., "Synthesis Of Some 2,3-Didehydro-2-Deoxysialic Acids Structurally Varied At C-4 And Their Behavior Towards Sialidase From Vibrio Cholerae", Liebigs Anns. Chemie, 1991, No. 2 pp. 129–134.

Zbiral et al., "Synthesis Of the 4-acetamido-4-deoxy analogue of N-acetylneuraminic and its behaviour towards CMP-sialate synthase", Carbohydrate Research, vol. 194, 1989, pp. C15–C18.

*Primary Examiner*—Nicky Chan
*Attorney, Agent, or Firm*—Foley & Lardner

[57] ABSTRACT

N-Acetylneuraminic and derivatives of formula (I)

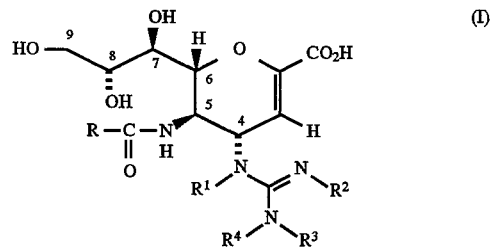

pharmaceutical formulations thereof, their use in medicine, in particular as antiviral agents and methods for their preparation are described.

11 Claims, No Drawings

ANTIVIRAL 4-SUBSTITUTED-2-DEOXY-2,3-DIDEHYDRO-DERIVATIVES OF α-D-NEURANINIC ACID

This application is a continuation, of application Ser. No. 07/984,124, filed Dec. 4, 1992, now abandoned.

This invention relates to a new class of chemical compounds and to their use in medicine. In particular the invention concerns new 4-substituted-2-deoxy 2,3-didehydro derivatives of α-D-neuraminic acid, methods for their preparation, pharmaceutical formulations thereof and their use as antiviral agents.

Enzymes with the ability to cleave N-acetyl neuraminic acid (NANA), also known as sialic acid, from other sugars are present in many microorganisms. These include bacteria such as Vibrio cholerae, Clostridium perfringens, Streptococcus pneumoniae, and Arthrobacter sialophilus, and viruses such as influenza virus, parainfluenza virus, mumps virus, Newcastle disease virus, fowl plague virus, and Sendai virus. Most of these viruses are of the orthomyxovirus or paramyxovirus groups, and carry a neuraminidase activity on the surface of the virus particles.

Many of the neuraminidase-possessing organisms are major pathogens of man and/or animals, and some, such as influenza virus, Newcastle disease virus, and fowl plague virus, cause diseases of enormous economic importance.

It has long been thought that inhibitors of neuraminidase activity might prevent infection by neuraminidase-bearing viruses. Most of the known neuraminidase inhibitors are analogues of neuraminic acid, such as 2-deoxy-2,3-didehydro-N-acetylneuraminic acid (DANA) and its derivatives. See, e.g., Meindl et al., Virology 1974 58 457–63. The most active of these is 2-deoxy-2,3-dehydro-N-trifluoroacetyl-neuraminic acid (FANA), which inhibits multi-cycle replication of influenza and parainfluenza viruses in vitro. See Palese et at., Virology 1974 59 490–498.

A number of 2-deoxy-2,3-didehydro-N-acetylneuraminic acid derivatives are known in the art (see for example P Meindl et al., Virology, 58, 457–463 (1974); P Meindl and H Tuppy, Mh. Chem, 100 (4), 1295–1306 (1969); M. Flashner et at., Carbohydrate Research 103, 2810785 (1982); E Zbiral et at., Liebigs Ann Chem 1989, 159–165; T Ogawa and Y Ito, Tetrahedron Letters 28(49), 6221–6224 (1987); T. Goto et al., Tetrahedron Letters 27(43), 5229–5232 (1986); H. Ogura et al., Chem. Pharm. Bull 36 (12), 4807–4813 (1988); German Offenlegungschrift P 1439249. Many of these compounds are active against neuraminidase from V. cholerae or Newcastle disease virus as well as that from influenza virus. Neuraminidase in at least some strains of influenza or parainfluenza viruses has also been reported to be inhibited by 3-aza-2,3,4-trideoxy-4-oxo-D-arabinoctonic acid δ-lactone and O-α-N-acetyl-D- neuraminosyl-) 2→3)-2-acetamido-2-deoxy-D-glucose Zakste'skaya et al., Vop. Virol. 1972 17 223–28.

Neuraminidase from Arthrobacter sialophilus is inhibited by the glycols 2,3-dehydro-4-epi-N-acetyl-neuraminic acid, 2,3-dehydro-2- deoxy-N-acetylneuraminic acid and 5-acetamido-2,6-anhydro-2,3,5- trideoxy-D-mannonon-2-en-4-ulosonate, and by their methyl esters. See Kumar et al., Carbohydrate Res. 1981 94 123–130; Carbohydrate Res. 1982 103 281–285. The thio analogues 2-α-azido-6-thioneuraminic acid and 2,3-dehydro-6-thioneuraminic acid, Mack & Brossmer, Tetrahedron Letters 1987 28 191–194, and the fluorinated analogue N-acetyl-2,3-difluoro-α-D-neuraminic acid, Nakajima et al., Agric. Biol. Chem 1988 52 120–1215, were reported to inhibit neuraminidase, although the type of neuraminidase was not identified. Schmid et al., Tetrahedron Letters 1958 29 3643–3646, described the synthesis of 2-deoxy-N-acetyl-α-D-neuraminic acid, but did not report its activity or otherwise against neuraminidase.

None of the known inhibitors of neuraminidase activity in vitro has been shown to possess antiviral activity in vivo, and indeed some, such as FANA, have specifically been shown to be inactive in vivo. Thus the conventional wisdom has accordingly considered that compounds exhibiting in vitro inhibition of viral neuraminidase would not effect an in vivo blockade of virus infection.

Meindl and Tuppy, Hoppe-Seyler's Z. Physiol Chem. 1969 350 1088, described hydrogenation of the olefinic double bond of 2- deoxy-2,3-dehydro-N-acetylneuraminic acid to produce the β-anomer of 2-deoxy-N-acetylneuraminic acid. This β-anomer did not inhibit Vibrio cholerae neuraminidase.

The most potent in vitro inhibitors of vital neuraminidase have thus been identified as compounds that are based on the neuraminic acid framework, and these are thought by some to be transition-state analogues. Miller et al., Biochem. Biophys. Res. Comm. 1978 83 1479. But while many of the aforementioned neuraminic acid analogues are competitive inhibitors of neuraminidase, to date, none has been reported as showing anti-viral activity in vivo. For example, although a half-planar, unsaturated 6-member ring system has been asserted to be important for inhibitory activity, see Dernick et al. in ANTIVIRAL CHEMOTHERAPY (K. K. Gauri ed.) Academic Press, 1981, at pages 327–336, some compounds characterized by such a system, notably FAN& have been reported not to possess in vivo anti-viral activity. See Palese and Schulman in CHEMOPROPHYLAXIS AND VIRUS INFECTION OF THE UPPER RESPIRATORY TRACT, Vol. 1 (J. S. Oxford ed.) CRC Press, 1977, at pages 189–205.

We have now found a novel class of 4-substituted 2,3-didehydro derivatives of α-D-neuraminic acid which are unexpectedly more active than their corresponding 4-hydroxy analogues and which are active in vivo.

The invention therefore provides in a first aspect compounds of formula (I)

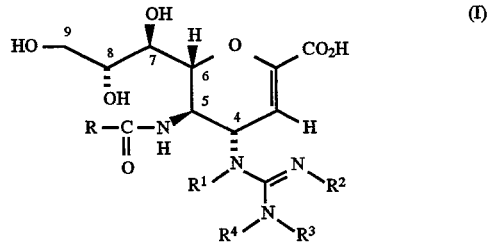

wherein

R is hydrogen or substituted or unsubstituted $C_{1-6}$alkyl (e.g. methyl, ethyl) or aryl (e.g. phenyl); and $R^1$, $R^2$, $R^3$ and $R^4$, which may be the same or different, are hydrogen, substituted or unsubstituted $C_{1-6}$alkyl (e.g. methyl, ethyl), $C_{3-8}$cycloalkyl (e.g. cyclopentyl) or $C_{1-6}$alkoxy (e.g. methoxy, ethoxy), substituted or unsubstituted aryl (e.g. phenyl) or aralkyl (e.g. phen$C_{1-3}$alkyl such as benzyl), substituted or unsubstituted aryloxy (e.g. phenoxy) or aralkyloxy (e.g. phen$C_{1-3}$alkoxy such as benzyloxy), amino, hydroxy, cyano, nitro, $COR^5$, $CO_2R^5$ or $SO_2R^5$ (in which $R^5$ is hydrogen or substituted or unsubstituted $C_{1-6}$alkyl or aralkyl) or $CONR^6R^7$ (in which $R^6$ and $R^7$, which may be the same or different, are hydrogen or substituted or unsubstituted $C_{1-6}$alkyl or aralkyl), or R³ and R⁴, together with the attached nitrogen atom, form a saturated or unsaturated monocyclic 5 to 7-membered ring (e.g. piperidine, pyrrolidine) which optionally contains an additional heteroatom (such as nitrogen, oxygen or sulphur), or R¹ and at least one of R³ and R⁴, together with the attached N-C-N chain, form a saturated or unsaturated monocyclic 5 to 7-membered ring (e.g. imidazole) which optionally contains an additional heteroatom (such as nitrogen, oxygen or sulphur), or R² and at least one of R³ and R⁴, together with the attached N=C—N chain, form an unsaturated monocyclic 5 to 7-membered ring (e.g. imidazole) which optionally contains an additional heteroatom (such as nitrogen, oxygen or sulphur), with the proviso that at least one of R¹, R², R³ and R⁴ is other than hydrogen, and pharmaceutically acceptable salts of the compounds of formula (I) and pharmaceutically acceptable derivatives thereof.

In the compounds of formula (I) the substituents may themselves bear substituents conventionally associated in the art of pharmaceutical chemistry with such substituents.

$C_{1-6}$alkyl and alkoxy as used herein includes both straight chain (e.g. methyl, methoxy, ethyl, ethoxy) and branched chain (e.g. isopropyl, isopropoxy, t-butyl) alkyl and alkoxy groups.

Preferably R is methyl or halogen substituted methyl (e.g. $FCH_2$, $F_2CH-$, $F_3C$).

Preferably R¹, R², R³ and R⁴, which may be the same or different, are hydrogen, $C_{1-4}$alkyl (e.g. methyl), amino, hydroxy, cyano, $C_{1-4}$alkoxycarbonyl or nitro, with the proviso that at least one of R¹, R², R³ and R⁴ is other than hydrogen.

In a particularly preferred group of compounds of formula I R is methyl; R¹ is hydrogen; and one of R², R³ and R⁴ is methyl, amino, hydroxy, cyano or nitro and the others are hydrogen. Within this group R¹, R³ and R⁴ are preferably all hydrogen.

It will be appreciated by those skilled in the art that the compounds of formula (I) may exist in tautomeric forms. The present invention includes compounds of formula (I) and tautomers thereof.

It will be appreciated by those skilled in the art that in formula (I) the stereochemistry is absolute at positions C4, C5 and C6 but shows only the relative stereochemistry of the two OH groups at positions C7 and C8.

By pharmaceutically acceptable derivative is meant any pharmaceutically acceptable ester or salt of such ester of the compounds of formula (I) or any other compound which upon administration to the recipient is capable of providing (directly or indirectly) a compound of formula (I) or an antivirally active metabolite or residue thereof.

It will be appreciated by those skilled in the art that the compounds of formula (I) may be modified to provide pharmaceutically acceptable derivatives thereof at any of the functional groups in the compounds. Of particular interest as such derivatives are compounds modified at the C-1 carboxyl function, the C-7 or C-9 hydroxyl functions or at amino groups. Thus compounds of interest include C-1 alkyl (such as methyl, ethyl or propyl e.g. isopropyl) or aryl (e.g. phenyl, benzoyl) esters of the compounds of formula (I), C-7 or C-9 esters of compounds of formula (I) such as acetyl esters thereof, C-7 or C-9 ethers such as phenyl ethers, benzyl ethers, p-tolyl ethers and acylated amino derivatives such as formyl, acetamido.

It will be appreciated by those skilled in the art that the pharmaceutically acceptable derivatives of the compounds of formula (I) may be derivatised at more than one position.

It will also be appreciated by those skilled in the art that compounds of formula (I) containing certain combinations of substituents R¹, R², R³ and R⁴ may be unstable or difficult to synthesise, for example where R³ and R⁴ are both hydroxy. Pharmaceutically acceptable derivatives of such compounds may be more stable or more readily synthesised and are preferred.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, naphthalene-2-sulphonic and benzenesulphonic acids. Other acids such as oxalic, while not in themselves pharmaceutically acceptable may be useful in the preparation of salts useful as intermediates in obtaining compounds of the invention and their pharmaceutically acceptable acid addition salts.

Salts derived from appropriate bases include alkali metal (e.g. sodium), alkaline earth metal (e.g. magnesium), ammonium and $NR_4^+$ (where R is $C_{1-4}$alkyl) salts.

References hereinafter to a compound of the invention includes the compounds of formula (I) and pharmaceutically acceptable salts and derivatives thereof.

It will be appreciated by those skilled in the art that the nomenclature of the compounds of formula can be defined in a number of ways. The compounds of formula (I) are, generically, 4-substituted analogues of 2-deoxy-2,3-didehydro-N-acetylneuraminic acid; thus following names are synonymous:

5-(Acetylamino)-4-substituent-2,6-anhydro-3,4,5-trideoxy-D-glycero-D-galacto-non-2-enonic acid

=

5-Acetamido-4-substituent-2,3,4,5-tetradeoxy-D-glycero-D-galacto-non-2-enopyranosonic acid

=

Preferred compounds of the invention include:

5-(Acetylamino)-4-[[amino(methylimino)methyl]amino]-2,6-anhydro-3,4,5-trideoxy-D-glycero-D-galacto-non-2-enonic acid;

5-(Acetylamino)-4-[[amino(aminoimino)methyl]amino]-2,6-anhydro-3,4,5-trideoxy-D-glycero-D-galacto-non-2-enonic acid;

5-(Acetylamino)-4-[[amino(nitroimino)methyl]amino]-2,6-anhydro-3,4,5-trideoxy-D-glycero-D-galacto-non-2-enonic acid;

5-(Acetylamino)-4-[[amino(hydroxyimino)methyl]amino]-2,6-anhydro-3,4,5-trideoxy-D-glycero-D-galacto-non-2-enonic acid; and 5-(Acetyl amino)-4-[[amino](ethoxycarbonylimino)methyl]amino]-2,6-anhydro-3,4,5-trideoxy-D-glycero-D-galacto-non-2-enonic acid; tautomers thereof and pharmaceutically acceptable salts and derivatives thereof.

The compounds of formula (I) possess antiviral activity. In particular these compounds are inhibitors of viral neuraminidase of orthomyxoviruses and paramyxoviruses in particular neuraminidase, for example the viral neuraminidase of influenza A and B, parainfluenza, mumps and Newcastle disease.

There is thus provided in a further aspect of the invention a compound of formula (I) or a pharmaceutically acceptable salt or derivative thereof for use as an active therapeutic agent in particular as an antiviral agent for example in the treatment of orthomyxovirus and paramyxovirus infections.

In a further or alternative aspect there is provided a method for the treatment of a vital infection, for example orthomyxovirus and paramyxovirus infections in a mammal including man comprising administration of an effective amount of a compound of formula (I) or a pharmaceutically acceptable salt or derivative thereof.

There is also provided in a further or alternative aspect use of a compound of the invention for the manufacture of a medicament for the treatment of a viral infection.

It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient and will ultimately be at the discretion of the attendant physician or veterinarian. In general however a suitable dose will be in the range of from about 0.1 to 750 mg/kg of bodyweight per day, preferably in the range of 0.5 to 60 mg/kg/day, most preferably in the range of 1 to 20 mg/kg/day.

Treatment is preferably commenced before or at the time of infection and continued until virus is no longer present in the respiratory tract. However the compounds are also effective when given post-infection, for example after the appearance of established symptoms. Suitably treatment is given 1–4 times daily and continued for 3–7, e.g. 5 days post infection depending upon the particular compound used.

The desired dose may be presented in a single dose or as divided doses administered at appropriate intervals, for example as two, three, four or more sub-doses per day.

The compound is conveniently administered in unit dosage form for example containing 10 to 1500 mg, conveniently 20 to 1000 mg, most conveniently 50 to 700 mg of active ingredient per unit dosage form.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (1) or a pharmaceutically acceptable salt or derivative thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carders as are known in the art to be appropriate.

For intranasal administration according to the method of the invention the neuraminidase inhibitors may be administered by any of the methods and formulations employed in the art for intranasal administration.

Thus in general the compounds may be administered in the form of a solution or a suspension or as a dry powder.

Solutions and suspensions will generally be aqueous for example prepared from water alone (for example sterile or pyrogen-free water) or water and a physiologically acceptable co-solvent (for example ethanol, propylene glycol, polyethlene glycols such as PEG 400).

Such solutions or suspensions may additionally contain other excipients for example preservatives (such as benzalkonium chloride), solubilising agents/surfactants such as polysorbates (e.g. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomising spray pump.

Intranasal administration may also be achieved by means of an aerosol formulation in which the compound is provided in a pressurised pack with a suitable propellant such as a chlorofluorocarbon (CFC) for example dichlorodifluoromethane, trichlorofluoromethane or dichlorotetrafluroroethane, carbon dioxide or other suitable gas. The aerosol may conveniently also contain a surfactant such as lecithin. The dose of drug may be controlled by provision of a metered valve.

Alternatively the compounds may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In the intranasal formulations the compound will generally have a small particle size for example of the order of 5 microns or less. Such a particle size may be obtained by means known in the art, for example by micronisation.

When desired, formulations adapted to give sustained release of the active ingredient may be employed.

The compounds of the invention may also be used in combination with other therapeutic agents, for example other anti-infective agents. In particular the compounds of the invention may be employed with other antiviral agents. The invention thus provides in a further aspect a combination comprising a compound of formula (I) or a pharmaceutically acceptable salt or derivative thereof together with another therapeutically active agent, in particular an antiviral agent.

The combinations referred to above may conveniently be presented for use in the form of a pharmaceutical formulation and thus such formulations comprising a combination as defined above together with a pharmaceutically acceptable carrier therefor comprise a further aspect of the invention.

Suitable therapeutic agents for use in such combinations include other anti-infective agents, in particular antibacterial and anti-vital agents such as those used to treat respiratory infections. For example, other compounds effective against influenza viruses, such as amantadine, rimantadine and ribavirin, may be included in such combinations.

The individual components of such combinations may be administered either sequentially or simultaneously in separate or combined pharmaceutical formulations.

When the compounds of the invention are used with a second therapeutic agent active against the same virus the dose of each compound may either be the same as or differ from that employed when each compound is used alone. Appropriate doses will be readily appreciated by those skilled in the art.

Compounds of formula (I) and pharmaceutically acceptable salts and derivatives thereof may be prepared by the methods outlined below which methods form a further aspect of the invention. In the following processes R, $R^1$, $R^2$, $R^3$ and $R^4$ are as defined for formula (I) unless otherwise specified.

According to one general process a compound of formula (I) may be prepared by the reaction of a compound of formula (II)

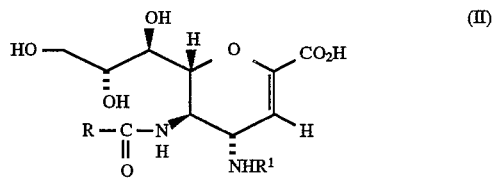

with a compound of formula (III)

wherein

L is a leaving group such as for example $SO_3H$, $SCH_3$, pyrazole, 3,5-dimethylpyrazole or cyanamide. The reaction will generally be effected in an aqueous medium in the presence of a base, for example an alkali metal carbonate such as sodium carbonate. Alternatively compounds of formula (I) may be prepared by reaction of a compound of formula (II) wherein $R^1$ is cyano with an amine $R^2NH_2$.

Compounds of formula (II) may be prepared by derivatisation of a compound of formula (IV)

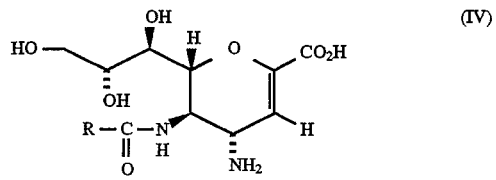

for example by Eschweiler-Clark alkylation (e.g. methylation).

The compounds of formula (IV) are either known in the art (see, for example, Liebigs Ann. Chem. 1991, 129–134) or may be obtained by methods analogous to those for preparing the known compounds.

Compounds of formula (III) wherein L is $SO_3H$ may be prepared by oxidation of a compound of formula (V)

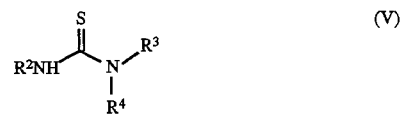

for example by heating in the presence of an oxidant such as a peroxy acid (e.g. peracetic acid) in a suitable anhydrous solvent such as acetic anhydride.

Compounds of formula (V) are either known compounds or may be prepared from known compounds by methods analogous to those for preparing the known compounds.

As will be appreciated by those skilled in the art it may be necessary or desirable at any stage in the above described processes to protect one or more sensitive groups in the molecule to prevent undesirable side reactions; the protecting group may be removed at any convenient subsequent stage in the reaction sequence.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene (John Wiley and Sons 1981).

Conventional amino protecting groups may include for example aralkyl groups, such as benzyl, diphenylmethyl or triphenylmethyl groups; and acyl groups such as N-benzyloxycarbonyl or t- butoxycarbonyl. Thus, compounds of general formula (I) wherein one or both of the groups $R^3$ and $R^4$ represent hydrogen may be prepared by deprotection of a corresponding protected compound.

Hydroxy groups may be protected, for example, by aralkyl groups, such as benzyl, diphenylmethyl or triphenylmethyl groups, acyl groups, such as acetyl, silicon protecting groups, such as trimethylsilyl groups, or as tetrahydropyran derivatives.

Removal of any protecting groups present may be achieved by conventional procedures. Thus an aralkyl group such as benzyl, may be cleaved by hydrogenolysis in the presence of a catalyst (e.g. palladium on charcoal); an acyl group such as N-benzyloxycarbonyl may be removed by hydrolysis with, for example, hydrogen bromide in acetic acid or by reduction, for example by catalytic hydrogenation; silicon protecting groups may be removed, for example, by treatment with fluoride ion; tetrahydropyran groups may be cleaved by hydrolysis under acidic conditions.

Where it is desired to isolate a compound of the invention as a salt, for example as an acid addition salt, this may be achieved by treating the free base of general formula (I) with an appropriate acid, preferably with an equivalent amount, or with creatinine sulphate in a suitable solvent (e.g. aqueous ethanol).

The present invention is further described by the following examples which are for illustrative purposes only and should not be construed as a limitation of the invention.

EXAMPLE 1

5-(Acetylamino)-4-[[amino(aminoimino)methyl]amino]-2,6-anhydro-3,4,5-trideoxy-D-glycero-D-galacto-non-2-enonic acid (i) 5-(Acetylamino)-4-cyanoamino-2,6-anhydro-3,4,5-trideoxy-D-glycero-D-galacto- non-2-enonic acid 5-(Acetylamino)-4-amino-2,6-anhydro-3,4,5-trideoxy-D-glycero-D-galacto-non-2-enonic acid (3 g, 10.35 mmol) was suspended in methanol (37.5 ml) and sodium acetate (1.89 g, 23.1 mmol) was added, causing a "caking" of the suspension and making stirring difficult. To this at 21° C. with exclusion of moisture was added a solution of cyanogen bromide (1.14 g, 10.8 mmol) in methanol (150 ml), in a dropwise manner. Stirring gradually became easier, until a readily stirrable suspension was obtained. Addition was complete in 3.5 hr. The mixture was then stirred at 21° C. with exclusion of moisture for 44 hr. The small amount of remaining solid was filtered off and solvent evaporated in vacuo to an orange-brown foam. The foam was taken up in methanol (125 ml) and with rapid stirring at 21° C. was treated dropwise with propan-2-ol (130 ml). The precipitate was filtered off, washed with iPrOH:MeOH 3:2, and combined filtrate and washings evaporated to give the title compound as a pale yellow foam (3.48 g).

Analytical Data.

$^1$H NMR: (D$_2$O) δ5.65(1H, s H3) 4.30(1H, d, H4), 4.18(1H, d, H6), 4.07(1H, t, H5), 3.90(2H, m, H7,H8), 3.65(2H, m, H9), 2.08(3H, s, acetyl) ppm.

IR: (KBr) ν 3300 (bd), 2224 (CN) cm$^{-1}$.

(ii) 5-(Acetylamino)-4-[[amino(aminoimino)methyl]amino]-2,6-anhydro-3,4,5-tri deoxy-p-glycero-D-galacto-non-2-enonic acid The product of step (i) (500 mg, 1.59 mmol) was dissolved in dried (over 3 A mol. sieves) methanol (20 ml) and anhydrous hydrazine (0.5 ml, 15.9 mmol) was added. This was then stirred at 21° C. for 18 hr. The white precipitate was filtered off, washed with methanol and air-dried (0.172 g, 31%). The solid was taken up in water (3.2 ml) and with warming and swirling, propan-2-ol (8.1 ml) was added. The cystallised material was filtered off, air-dried then dried under high vacuum to give the title compound as a white solid (0.127 g,).

Analytical Data:

$^1$H NMR: (D$_2$O) δ: 5.62(1H, d, H3), 4.47(1H, dd, H4), 4.39(1H, d, H6), 4.25(1H, dd, H5), 3.99–3.85(2H, m, H7,H8), 3.69–3.60(2H, m, H9), 2.03(3H, s, acetyl) ppm.

IR: (Nujol): ν3234, 2952, 1685, 1667, 1653, 1619, 1571, 1456, 1411, 1372, 1321, 1275 cm$^{-1}$.

UV: (H$_2$O): $\lambda_{max}$=234, $E^1_1$=206.2.

MA: $C_{12}H_{21}N_5O_7$. 0.2H$_2$O Requires: C 41.06, H 6.15, N 19.96%. Found: C40.82, H 5.80, N 19.76%.

CZE:>97% purity.

M.Pt.: ($M^2_{60}$)>180°

EXAMPLE 2

5-(Acetylamino)-4-[[amino(hydroxyimino)methyl]amino]-2,6-anhydro-3,4,5-trideoxy-D-glycero-D-galacto- non-2-enonic acid Hydroxylamine hydrochloride (1.1 g, 15.85 mmol)(dried under vacuum over P$_2$O$_5$) was dissolved in dried (over 3 A mol. sieves) methanol (20 ml) and sodium carbonate (0.835 g, 7.9 mmol) was added. This was stirred at 21° C. under N$_2$ for 15 min., then solid was filtered off. To the filtrate was then added the product of Example 1, step (i) (500 mg, 1.585 mmol) and stirring under N$_2$ at 21° C. continued for 16 hr. White solid was filtered off, air dried, then dried under high vacuum to give the title compound (Yield, 180 mg).

Analytical Data.

$^1$H NMR: (D$_2$O) δ: 5.62(1H, d, H3), 4.48(1H, dd, H4), 4.38(1H, d, H6), 4.27(1H, dd, H5), 3.98–3.86(2H, m, H7,H8), 3.70–3.60(2H, m, H9), 2.02(3H, s, acetyl) ppm.

IR: (nujol) ν3238, 3088, 3924, 1626, 1554, 1457, 1402, 1376, 1322 cm$^{-1}$.

UV: (H2O ) $\lambda_{max}$=234 nm, $E^1_1$=154.1

MA. $C_{12}H_{20}N_4O_8$. 1.6NaCl. 0.5H$_2$ Requires C31.97,H 4.69, N 12.43, Cl 12.58% Found: C 31.60, H 4.84, N 12.40, Cl 12.40%.

CZE: 97.9% purity.

EXAMPLE 3

5-(Acetylamino)-4[[amino(methylimino )methyl]amino]-2.6-anhydro-3,4,5-trideoxy-D-galacto-non-2-enonic acid 5-(Acetylamino)-4-cyanoamino-2,6-anhydro-3,4,5-trideoxy-D-glycero-D-galacto-no n-2- enopyranosonic acid (500 mg, 1.585 mmol) was dissolved in dried (over 3 A mol. sieves) methanol (12ml) and methylamine (33 wt. % solution in ethanol, 1.93 ml, 15.85 mmol) was added. This was stirred at 21° C. for 18 hr. The precipitate was filtered off and air dried to a white solid (127 mg, 23%). This was recrystallised from water (1.4 ml) and propan-2-ol (6.9 ml). The product was filtered off and dried under high vacuum to give the title compound as a white solid (56 mg, 10.2%). Concentration of mother liquors gave a further 21.3 mg (4%) of product.

Analytical Data $^1$H NMR: (D$_2$O) δ: 5.62(1H, d, H3), 4.46(1H, dd, H4), 4.38(1H, d, H6), 4.24(1H, dd, H5), 3.98–3.90(2H, m, H7+H8), 3.70–3.60(2H, m, H9), 2.83(3H, s, NHMe), 2.01 (3H, s, NHCOMe) ppm.

IR: (Nujol): ν2953, 2923, 2853, 1633, 1463, 1376 cm$^{-1}$.

UV: (H$_2$O): $\lambda_{max}$=235 nm, $E_1^1$=197.8.

MA: $C_{13}H_{22}N_4O_7$. O6H$_2$O Requires: C 43.72, H 6.54, N 15.69%. Found: C 43.71, H 6.59, N 15.51%.

CZE: 97.7% purity.

M.Pt.: ($M^2{}_{60}$)>180° C.

EXAMPLE 4

5-(Acetylamino)-4-[[amino(nitroimino)methyl]amino]-2,6-anhydro-3,4,5-trideoxy-D-glycero-D-galacto-2-enonic acid (i) 2-Methyl-1-nitro-2-thiopseudourea 2Methyl-2-thiopseudouronium sulfate (1) (2 g, 7.18 mmol) was added portionwise over 10 min. to a nitrating mixture of 2 ml of fuming nitric acid and 6 ml of 98% sulfuric acid. The nitration was carried out at −10° C. for addition of half of the reacting substance, then at 0° C. to +5° C. for the remainder. The solution was then recooled to 0° C. and poured onto ice (85 g). The precipitate was filtered off, washed with water (15 ml) then air dried This was recrystallised from ethanol/water 1:2 (50 ml) to give title compound as a white crystalline solid (1.18 g).

Analytical Data:

$^1$H NMR: (DMSO): δ: 9.12(2H, s(bd), NH$_2$), 2.40(3H, s, CH$_3$) ppm.

IR: (DMSO): ν1647, 1528, 1487, 1455, 1294, 1254 cm$^{-4}$.

UV: (Ethanol): $\lambda_{max}$=279 nm, $E_1^1$=968.

MA: $C_2H_5N_3O_2S$ Requires: C17.77, H3.73, N31.10, S 23.72%. Found: C17.31 H 3.60, N 30.70, S 23.57%.

M.Pt.: ($M^2{}_{80}$) 164.5° C.

(ii) 5-(Acetylamino)-4-[[amino(nitroimino)methyl]amino]-2,6-anhydro-3,4,5-trideoxy-D-glycero-D-galacto-non-2-enonic acid 5-(Acetylamino)-4-amino-2,6-anhydro-3,4,5-trideoxy-D-glycero-D-galacto-non-2-enonic acid (200 mg, 0.689 mmol) was dissolved in absolute methanol (2.7 ml) by the addition of triethylamine (0.098 ml, 0.690 mmol). 2-Methyl-1-nitro-2-thiopseudourea (103 mg,0.757 mmol) was then added. The mixture was warmed to 40° C. with stirring under nitrogen for 2hrs, then stirred at 21° C. for 16 hr. The addition of reagent and heating and stirring was repeated twice more. The cooled mixture was then filtered and the white solid washed with methanol. Combined filtrate and washings were evaporated and the residue purified by ion exchange chromatography (Dowex 50 W×8(H+) resin, eluting with water. Appropriate fractions were combined and freeze dried. The residue was triturated with warm water (4 ml), and the off-white solid filtered and dried under high vacuum to give the title product (Yield =50 mg).

Analytical Data:

$^1$H NMR: (D$_2$O): δ: 5.95(1H, d, H3), 4.80(1H, m, H4), 4.45(1H, d, H6), 4.25(1H, t, H5), 3.85–4.00(2H, m, 0.5H9+H8), 3.60–3.75(2H, m, 0.5H9+H7), 200(3H, s, Ac) ppm.

$^{13}$C NMR: (D$_2$O): 21.8(Ac CH$_3$), 47.5(C5), 50.0(C4), 63.0(C9), 67.9(C7), 69.9(C8), 75.9(C3), 144(C2), 159.4 (guanidino), 174.5(Cl), 188.9(Ac C=O).

IR: (DMSO): ν1260 cm$^{-1}$ (NO$_2$).

UV: $\lambda_{max}$=272 nm, $E_1^1$=404.9

MA: $C_{12}H_{19}N_5O_9$.2H$_2$O Requires: C 34.86, H 5.61, H 5.61, N 16.95%. Found C 34.84, H 5.11, N 17.00%

CZE:>91% purity.

M.Pt:>230° C. (dec.)

EXAMPLE 5

5-Acetylamino)-4-[[amino(ethoxycarbonylimino)methyl] amino]-2,6-anhydro-3,4,5-trideoxy-D-glycero-D-galacto-non-2-enonic acid (i) 2-Methyl-1-ethoxycarbonyl-2-thiopseudourea To a solution of sodium ethoxide in ethanol (made by addition of sodium (0.155 g, 6.7 mmol) to dry ethanol(15 ml)) was added methyl iodide (1.47 ml, 23.6 mmol) followed by N-carbethoxythiourea (1.0 g, 6.7 mmol). The resulting solution was stirred at 21° C. under nitrogen for 1 hr. This was then treated with ether (32 ml) and the resultant precipitate filtered off. The filtrate was evaporated to a clear syrup, which crystallised at 0–4° C. to give the title compound as a white solid (0.815 g).

Analytical Data:

$^1$H NMR: (DMSO): δ8.62(2H, s, NH$_2$), 4.0(2H, q, J=7 Hz, CH$_2$), 2.32(3H, s, SCH$_3$), 1.18(3, t, J=7 Hz, CH$_3$) ppm.

IR: (Nujol): ν: 3338, 1663, 1593 cm$^{-4}$ (ii) 5-(Acetylamino)-4-[[amino(ethoxycarbonylimino) methyl]amino]-2,6-anhydro-3,4,5-trideoxy-D-glycero-non-2-enonic acid 5-(Acetylamino)-4-amino-2,6-anhydro-3,4,5-trideoxy-D-glycero-D-galacto-non-2-enonic acid (200 mg, 0.69 mmol) was dissolved in methanol (2.7 ml) by the addition of triethylamine (0.098 ml, 0.69 mmol). To this was added 2-methyl-1-ethoxycarbonyl- 2-thiopseudourea (112 mg, 0.69 mmol), the resulting solution heated at 50° C. for 5 hr. and then stirred at 21° C. for 16 hr. This process was repeated 3 more times and then stirred at 50° C. for 3 days more. The whole was then evaporated to dryness, redissolved in methanol (4 ml) and purified by preparative TLC, eluting with n-butanol/acetic acid/water 3:1:1. Appropriate fractions silica by stirring in methanol. The suspension was filtered to remove silica, then evaporated to a gum. This was triturated with ethyl acetate, stirring vigorously for 1 hr., and the off-white solid filtered and dried under high vacuum to give the title product (85 mg, 31%).

Analytical Data:

$^1$H NMR:(D$_2$): δIncludes: 5.62(1H, d, H3), 4.62(1H, m, H4), 4.45–4.25(4H, m, H5+H6+Et CH$_2$), 3.99–3.87(2H, m, 0.5H 9+H8), 3.69–3.60(2H, m, 0.5 H9+H7), 1.95(3H, s, Ac), 1.30(3H, t, Et CH$_3$) ppm.

MS: m/z: 405(MH$^+$), 427(MNa$^+$).

IR: (Nujol): ν2953, 2924, 2853, 1581, 1461, 1377 cm$^{-4}$.

UV: (EtOH): $\lambda_{max}$=227 nm, $E_1^1$=244.

CZE:>92% purity.

$[\alpha]_D^{20}$: +19.3°.

M.Pt.: ($M^2{}_{60}$): 232° C. (dec.).

EXAMPLE 6

Biological Activity

The compounds of Examples 1 to 5 were examined for their ability to inhibit in vitro N2 influenza neuraminidase and influenza virus replicaiton. The results are shown in Table 1.

The test methods were as follows:

(a) In vitro assay against N2 influenza neuraminidase Values for $K_{50}$ were measured via a spectrofluorometric technique which uses the fluorogenic substrate 4-methylumbelliferyl N-acetylneuraminic acid (MUN), as described by Meyers et al., Anal. Biochem. 1980 101 166–174. For both enzymes, the assay mixture contained test compound at several concentrations between 0 and 200 $\mu$ml$^{-1}$ in buffer (32.5 mM MES, 4 mM $CaCl_2$, pH 6.5 for N2;) using virion (X31) as the source of enzyme.

The reaction was started by the addition of MUN to final concentrations of 75 or 40 $\mu$M. After 15 minutes at 37° C. 15 $\mu$l of stop mix (5:1 EtOH:0.5M NaOH) was added to 5 $\mu$l reaction volume to terminate the reaction. Fluorescence was read at excitation 365 nm, emission 450 nm, and appropriate MUN blanks (containing no enzyme) were subtracted from readings. The $K_{50}$ was estimated from plots of % inhibition against $\log_{10}$[inhibitors].

(b) Inhibition of influenza virus replication in vitro

Inhibition of influenza A/Singapore/1/57 (H2N2) and influenza B/Victoria/102/85 replication in vitro was measured by reduction of vital plaque formation in Madin Darby canine kidney (MDCK) cells.

Monolayers of confluent MDCK cells, grown in six well tissue culture plates, were inoculated with 0.3 ml of virus diluted to give about 50–100 plaques/well. Virus was diluted in serum-free minimal essential medium (MEM) containing 2 $\mu$g/ml N-tosyl-1-phenylalanine chloromethyl ketone (TPCK) treated trypsin (Worthington Enzymes), and test compound.

Virus was adsorbed at room temperature for one hour, and the cells then overlaid with defined cell culture medium, version 1 (DCCM-1)/agar overlay containing test compound, 4 ml/well. DCCM-1 is a serum-free complete cell growth medium (Biological Industries), to which TPCK treated trypsin and DEAE-dextran to a final concentration of 2 $\mu$g/ml and 0.00% respectively, were added. Agar (5%) (Indubiose) was diluted 1:10 in the overlay before being added to the plate.

Once overlaid, plates were incubated at 37° C., 5% $CO_2$ for 3 days. Cells were then fixed with 5% glutaraldehyde, stained with carbol fuschin and the viral plaques counted.

TABLE I

| Compound of Example No. | NA1 ($\mu$g/ml) | $I_{50}$ Plaque Assay ($\mu$g/ml) Flu A | Flu B |
|---|---|---|---|
| 1 | 1.3 | 2.9 | 3.0 |
| 2 | 0.6 | 0.1 | <0.1 |
| 3 | 4.2 | 3.0 | NT |
| 4 | 1.0 | 30.0 | 24.0 |
| 5 | 6.9 | 1.7 | 0.6 |

EXAMPLE 7

Pharmaceutical Formulations

Intranasal Formulations

| (i) AQUEOUS SOLUTION | % w/w |
|---|---|
| Compound of formula (I) | 10.00 |
| Benzalkonium chloride | 0.04 |
| Phenylethyl alcohol | 0.40 |
| Purified water | to 100% w/w |

| | % w/w |
|---|---|
| (ii) AQUEOUS COSOLVENT SOLUTION | |
| Compound of formula (I) | 10.0 |
| Benzalkonium chloride | 0.04 |
| Polyethylene glycol 400 | 10.0 |
| Propylene glycol | 30.0 |
| Purified water | to 100% w/w |
| (iii) AEROSOL FORMULATION | |
| Compound of formula (I) | 7.5 |
| Lecithin | 0.4 |
| Propellant 11 | 25.6 |
| Propellant 12 | 66.5 |
| (iv) DRY POWDER FORMULATION | |
| Compound of formula (I) | 40.0 |
| Lactose | 60.0 |

These formulations are prepared by admixture of the active ingredient and excipients by conventional pharmaceutical methods.

We claim:

1. A compound of formula (I)

wherein

R is hydrogen, unsubstituted $C_{1-6}$alkyl, $C_{1-6}$ alkyl substituted by halogen or aryl and $R^1$ is H;

and one of $R^2$, $R^3$ and $R^4$, which may be the same or different, is methyl, amino, hydroxy, cyano, $C_{1-4}$alkoxycarbonyl, or nitro, and the others are hydrogen or a pharmaceutically acceptable salt or pharmaceutically acceptable ester or salt of said ester.

2. A compound as claimed in claim 1, wherein R is hydrogen, unsubstituted $C_{1-4}$alkyl, $C_{1-4}$alkyl substituted by halogen, or aryl.

3. A compound as claimed in claim 1 wherein R is methyl or halogen-subsituted methyl.

4. A compound as claimed in claims 1 wherein $R^1$, $R^3$ and $R^4$ are hydrogen and $R^2$ is methyl, amino, hydroxy, cyano, nitro, or $C_{1-4}$alkoxycarbonyl.

5. A compound selected from 5-(Acetylamino)-4-[[amino(methylimino)methyl]amino]-2,6-anhydro-3,4,5-trideoxy-D-glycero-D-galacto-non-2-enonic acid;

5-(Acetylamino)-4-[[amino(aminoimino)methyl]amino]-2,6-anhydro-3,4,5-trideoxy-D-glycero-D-galacto-non-2-enonic acid;

5-(Acetylamino)-4-[[amino(nitroimino)methyl]amino]-2,6-anhydro-3,4,5-trideoxy-D-glycero-D-galacto-non-2-enonic acid;

5-(Acetylamino)-4-[[amino(hydroxyimino)methyl]amino]-2,6-anhydro-3,4,5-trideoxy-D-glycero-D-galacto-non-2-enonic acid; and 5-(Acetylamino)-4-[[amino(ethoxycarbonylimino)methyl]amino]-2,6-anhydro-3,4,5-trideoxy-D-glycero-D-galacto-non-2-enonic acid;

or a pharmaceutically acceptable salt or pharmaceutically acceptable ester or salt of said ester.

6. A pharmaceutical formulation comprising a compound of formula (I) as defined claim 1 together with a pharmaceutically acceptable carrier therefor.

7. A method for the treatment of a mammal suffering from or susceptible to influenza, comprising administering a therapeutically effective amount of a compound according to claim 1.

8. A method according to claim 7, wherein R is hydrogen, unsubstituted $C_{1-4}$ alkyl, $C_{1-4}$ alkyl substituted by halogen, or aryl; and one of $R^2$, $R^3$ and $R^4$ is methyl, amino, hydroxy, cyano, $C_{1-4}$alkoxycarbonyl or nitro, and the others are hydrogen.

9. A method according to claim 7, wherein R is methyl or halogen-substituted methyl.

10. A method according to claim 7, wherein $R^1$, $R^3$ and $R^4$ are hydrogen ad $R^2$ is methyl, amino, hydroxy, cyano, nitro or $C_{1-4}$alkoxycarbonyl.

11. A method according to claim 7, wherein said compound is selected from the group consisting of 5-(Acetylamino)-4-[[amino(methylimino)methyl]amino]-2,6-anhydro-3,4,5-trideoxy-D-gylcero-D-galacto-non-2-enonic acid;

5-(Acetylamino)-4[[amino(aminoimino)methyl]amino]-2,6-anhydro-3,4,5-trideoxy-D-glycero-D-galacto-non-2-enonic acid;

5-(Acetylamino)-4[[amino(nitroimino)methyl]amino]-2,6-anhydro-3,4,5-trideoxy-D-glycero-D-galacto-non-2-enonic acid;

5-(Acetylamino)-4-[[amino(hydroxyimino)methyl]amino]-2,6-anhydro-3,4,5-trideoxy-D-glycero-D-galacto-non-2-enonic acid;

and 5-(Acetylamino)-4-[[amino(ethoxycarbonylimino)methyl]amino-2,6-anhydro-3,4,5-trideoxy-D-glycero-D-galacto-non-2-enonic acid;

or a pharmaceutically acceptable salt or pharmaceutically acceptable ester or salt of said ester.

* * * * *